(12) United States Patent  (10) Patent No.: US 7,795,465 B2
Zierke et al.  (45) Date of Patent: Sep. 14, 2010

(54) METHOD FOR PRODUCING SEMICARBAZONES

(75) Inventors: Thomas Zierke, Böhl-Iggelheim (DE); Stefan Engel, Nieder-Olm (DE); Peter Otto, Rödersheim-Gronau (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1041 days.

(21) Appl. No.: 10/592,271

(22) PCT Filed: Mar. 16, 2005

(86) PCT No.: PCT/EP2005/002802

§ 371 (c)(1), (2), (4) Date: Sep. 8, 2006

(87) PCT Pub. No.: WO2005/090293

PCT Pub. Date: Sep. 29, 2005

(65) Prior Publication Data

US 2007/0203356 A1  Aug. 30, 2007

(30) Foreign Application Priority Data

Mar. 17, 2004  (DE) ........................ 10 2004 013 083
Mar. 17, 2004  (EP) ................................. 04006413

(51) Int. Cl.
  *C07C 253/30*  (2006.01)
  *C07C 281/06*  (2006.01)
(52) U.S. Cl. ........................................ 558/417; 564/34
(58) Field of Classification Search ................. 558/417; 564/34

See application file for complete search history.

(56) References Cited

U.S. PATENT DOCUMENTS 5,288,727 A * 2/1994 Toki et al. .................... 514/632

FOREIGN PATENT DOCUMENTS

EP  0 462 456  12/1991
EP  0 500 111  8/1992

* cited by examiner

*Primary Examiner*—Peter G O'Sullivan
(74) *Attorney, Agent, or Firm*—Brinks Hofer Gilson & Lione

(57) ABSTRACT

The invention relates to a process for preparing semicarbazone compounds of the formula I, where $R^1$ and $R^2$ are each independently hydrogen, halogen, CN, $C_1$-$C_4$-alkyl, $C_1$-$C_4$-alkoxy, $C_1$-$C_4$-haloalkyl or $C_1$-$C_4$-haloalkoxy, and $R^3$ is $C_1$-$C_4$-alkoxy, $C_1$-$C_4$-haloalkyl or $C_1$-$C_4$-haloalkoxy, by reacting a hydrazone compound of the general formula II, where R is $C_1$-$C_4$-alkoxy, amino, $C_1$-$C_4$-alkylamino or di($C_1$-$C_4$-alkyl)amino, and $R^1$, $R^2$ are each as defined above, with an aniline compound of the general formula III where $R^3$ is as defined above.

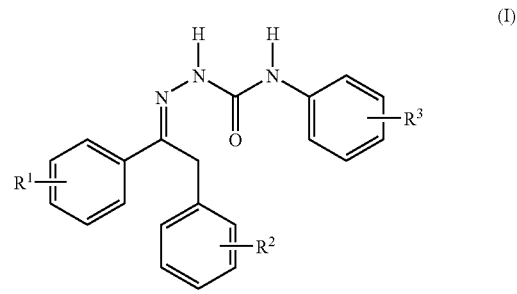

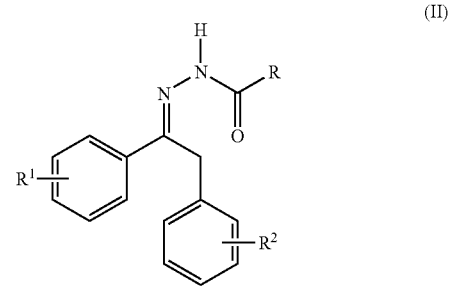

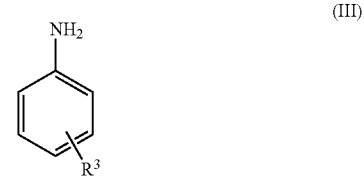

10 Claims, No Drawings

METHOD FOR PRODUCING SEMICARBAZONES

The present invention relates to a process for preparing semicarbazone compounds of the formula I

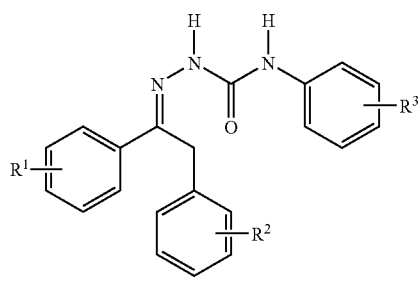

(I)

where $R^1$ and $R^2$ are each independently hydrogen, halogen, CN, $C_1$-$C_4$-alkyl, $C_1$-$C_4$-alkoxy, $C_1$-$C_4$-haloalkyl or $C_1$-$C_4$-haloalkoxy, and $R^3$ is $C_1$-$C_4$-alkoxy, $C_1$-$C_4$-haloalkyl or $C_1$-$C_4$-haloalkoxy.

EP-A 462 456 discloses compounds of the formula I as insecticides. They are prepared starting from benzyl phenyl ketones of the formula IV by the processes illustrated in Schemes 1 and 2:

Scheme 1

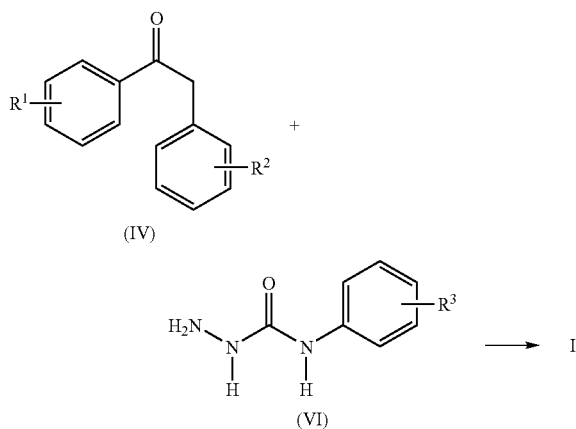

Scheme 2:

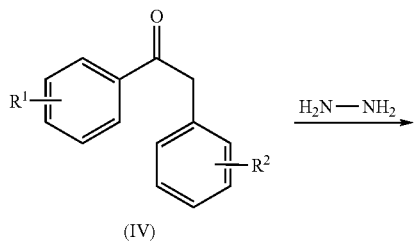

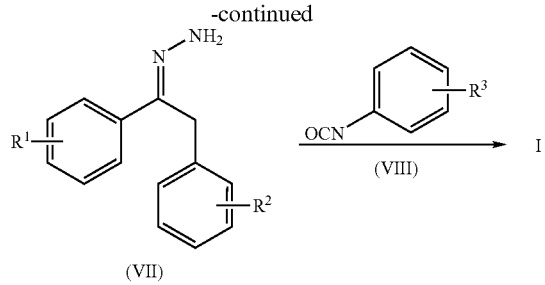

In Schemes 1 and 2, $R^1$, $R^2$ and $R^3$ are each as defined above.

However, the reaction, illustrated in Scheme 1, of a phenyl benzyl ketone IV with an N-phenyl semicarbazide VI only provides the compound I in poor yields. In addition, the semicarbazide VI has to be prepared in a separate reaction step from the corresponding aniline.

One disadvantage of the process illustrated in Scheme 2 is the use of hydrazine in the first reaction step, which has to be used in high excess to prevent by-product formation. As is well known, hydrazine is a potential carcinogen which additionally tends to spontaneous decomposition with gas formation on contact with metallic materials. It is therefore only possible to handle hydrazine on the production scale with a very high level of technical complexity for safety reasons. In addition, the disposal of the hydrazine wastes obtained in this reaction on the industrial scale is associated with a high level of complexity, since the chemical destruction of highly concentrated hydrazine solutions proceeds highly exothermically and releases considerable amounts of gas. The use of hydrazine thus constitutes a considerable cost factor for this process. A further disadvantage of the process shown in Scheme 2 is the use of phenyl isocyanates VIII which firstly, as a consequence of their toxicity, require special safety measures in their handling and, additionally, have to be prepared from the corresponding anilines in a separate reaction.

It is therefore an object of the present invention to provide a process for preparing semicarbazone compounds of the general formula I which affords the compound I in high yields and good purities, and which initially overcomes the disadvantages of the prior art outlined here.

It has been found that, surprisingly, semicarbazone compounds of the general formula I are obtained in good yields and with high purity when a hydrazone compound of the general formula II

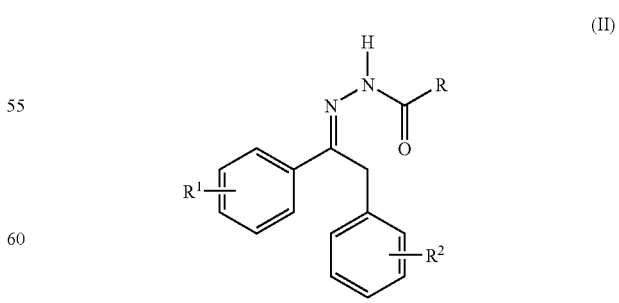

(II)

where R is $C_1$-$C_4$-alkoxy, amino, $C_1$-$C_4$-alkylamino or di($C_1$-$C_4$-alkyl)amino, and $R^1$, $R^2$ are each as defined above is reacted with an aniline compound of the general formula III

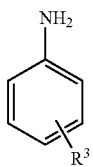

where $R^3$ is as defined above.

The present invention therefore provides a process for preparing semicarbazone compounds of the general formula I, comprising the reaction of a hydrazone compound of the general formula II with an substituted aniline of the formula III.

The hydrazone compounds of the general formula II may in turn be prepared in a similar manner to the known prior art processes from the benzyl phenyl ketones of the formula IV

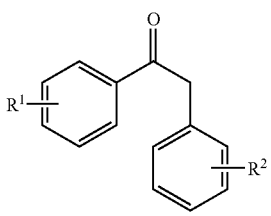

where $R^1$, $R^2$ are each as defined above by reacting IV with a hydrazide of the formula V

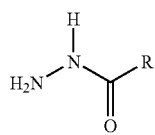

where R is as defined above. Accordingly, the process according to the invention preferably also comprises the preparation of the hydrazone compounds II by this route.

The hydrazone compounds of the formula II are novel where $R^2$=CN and likewise form part of the subject matter of the present invention as starting materials or intermediates in the process according to the invention.

In the definitions of the variables R, $R^1$, $R^2$ and $R^3$ specified in the above formulae, collective terms are used which are generally representative of particular substituents. The term $C_n$-$C_m$ specifies the number of carbon atoms in the particular substituents or substituent moiety which is possible in each case. Other definitions are as follows:

Halogen: fluorine, chlorine, bromine and iodine;

Alkyl and all alkyl moieties in alkoxy, alkylamino and dialkylamino: saturated, straight-chain or branched hydrocarbon radicals having from 1 to 4 carbon atoms such as methyl, ethyl, propyl, 1-methylethyl, butyl, 1-methylpropyl, 2-methylpropyl and 1,1-dimethylethyl (tert-butyl);

Haloalkyl and the haloalkoxy moieties in haloalkoxy: straight-chain or branched alkyl groups having from 1 to 4 and in particular 1 or 2 carbon atoms (as specified above), and some or all of the hydrogen atoms in these groups may be replaced by halogen atoms as specified above and in particular by fluorine (fluoroalkyl), for example chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2,2,3,3,3-pentafluoropropyl, heptafluoropropyl and 1,1,1-trifluoroprop-2-yl. Preferred haloalkyl is $C_1$-$C_2$-fluoroalkyl such as 2-fluoroethyl, 2,2-difluoroethyl, 2,2,2-trifluoroethyl, trifluoromethyl and difluoromethyl.

For the process according to the invention, it has been found to be particularly advantageous when R in formula II and accordingly also in formula V is $C_1$-$C_4$-alkoxy, in particular methoxy.

In another embodiment of the invention, R is $NH_2$, $C_1$-$C_4$-alkylamino or di($C_1$-$C_4$-alkyl)amino. R is then preferably amino ($NH_2$), methylamino, ethylamino or dimethylamino and is in particular $NH_2$.

The advantages of the process according to the invention become particularly apparent in the preparation of compounds of the formula I where the variables $R^1$, $R^2$ and $R^3$ are each independently defined as follows, more preferably in combination:

$R^1$ is $C_1$-$C_4$-haloalkyl, in particular trifluoromethyl and especially trifluoromethyl which is disposed in the meta-position (3-position) of the phenyl ring;

$R^2$ is cyano, in particular cyano which is disposed in the para-position (4-position);

$R^3$ is $C_1$-$C_4$-haloalkoxy, in particular trifluoromethoxy and especially trifluoromethoxy which is disposed in the para-position.

To react the aniline compound III with the hydrazone derivative II, the compounds will be used preferably in a molar III:II ratio in the range from 1:1.5 to 1.5:1, in particular from 1:1 to 1.3:1 and more preferably from 1.02:1 to 1.2:1.

The aniline compound III is advantageously reacted with the hydrazone compound II at temperatures above room temperature, for example in the range from 30 to 200° C., in particular from 50 to 180° C. and more preferably in the range from 70 to 150° C. The reaction pressure is of minor importance for the success of the process according to the invention and may be, for example, in the range from 500 mbar to 10 bar. Preference is given to carrying out the reaction in the region of atmospheric pressure, i.e. in the range from 0.9 to 1.2 bar. The reaction time required for the reaction is generally in the range from 1 h to 24 h and in particular in the range from 3 h to 12 h.

The reaction may in principle be carried out in substance. However, preference is given to reacting the aniline compound III with the hydrazone compound II in an organic solvent. Suitable solvents are in principle any which are capable of at least partly and preferably fully dissolving the compounds II and III under reaction conditions. Preferred solvents are aprotic. They are in particular those solvents that have a boiling point at atmospheric pressure in the range from 60 to 200° C. and in particular in the range from 80 to 150° C. Particularly preferred solvents are aromatic solvents, in particular alkylbenzenes such as toluene, xylenes, ethylbenzene, cumene (2-propylbenzene), cymenes (isopropyltoluenes) and mesitylene, and also chlorobenzenes, e.g. chlorobenzene, 1,2-, 1,3- and 1,4-dichlorobenzene, and also aliphatic nitriles such as acetonitrile and propionitrile and mixtures of these solvents.

The reaction of the aniline compound III with the hydrazone compound II may be carried out in the presence of an acid, although the use of an acid is not required. Examples of acids which are suitable in principle are sulfuric acid, organic sulfonic acids, in particular aromatic sulfonic acids such as p-toluenesulfonic acid and benzenesulfonic acid, aliphatic sulfonic acids such as methanesulfonic acid and trifluoromethanesulfonic acid, aromatic carboxylic acids such as benzoic acid and 4-trifluoromethylbenzoic acid, and aliphatic carboxylic acids having preferably from 1 to 3 carbon atoms, for example acetic acid and propionic acid. In general, the acid will be used in catalytic amounts, i.e. in amounts of less than 1 mol per mole of compound II or III, in particular less than 0.5 mol/mol and especially not more than 0.2 mol/mol. In a preferred variant of the process according to the invention, II is reacted with III in the absence of an acid.

At least some, preferably at least 50% and in particular at least 80%, of the compound R—H formed in the reaction of the aniline II with the hydrazone III will preferably be removed from the reaction mixture during the reaction, especially when the compound R—H is a $C_1$-$C_4$-alkanol such as methanol or ethanol. To this end, in the reaction will be carried out at a temperature and a pressure at which the compound R—H is distilled off, if appropriate as an azeotrope with the solvent from the reaction mixture. If appropriate, fresh solvent will be introduced into the reaction for compensation or the solvent which has been distilled off with the compound R—H is recycled into the reaction after, if appropriate, distillative depletion of the compound R—H. For these reasons, it is advantageous when the solvent used has a boiling point of at least 10 K and in particular at least 30 K above the boiling point of the compound R—H formed in the reaction (in each case at atmospheric pressure). Appropriately, the reaction of the compound II with the compound III is carried out in an apparatus which is equipped with at least one distillation and rectification apparatus, for example a distillation column, which firstly allows the compound R—H to be distilled off, if appropriate together with solvent, and simultaneously enables removal and recovery of any solvent distilled off with the compound R—H.

For the reaction, the compounds II and III may be contacted together in any manner. For example, the compounds II and III may be initially charged in a reaction vessel, if appropriate together with the desired solvent, and then the desired reaction conditions can be established. However, the majority or entirety of compounds II and III, if appropriate in a solvent, can be introduced into the reaction vessel under reaction conditions. In a preferred embodiment of the invention, the majority, especially at least 80% and more preferably the entirety or virtually the entirety (>95%) of the hydrazone compound II, if appropriate in the desired solvent, is initially charged and the majority, in particular at least 80% and more preferably the entirety or virtually the entirety (>95%) of the aniline compound is added thereto under reaction conditions in the course of the reaction, for example over a period of from 0.5 to 20 h and in particular from 1 to 10 h. To this end, the aniline compound III will preferably be dissolved in a solvent. If appropriate, the addition of the aniline compound III will be followed by a certain time, for example from 10 min to 10 h, in particular from 20 min to 5 h, of continued reaction.

The compound I can be isolated from the reaction mixture in a manner known per se. If the reaction has been carried out in a solvent, the reaction mixture will generally be concentrated and/or cooled, and/or a precipitant will be added. Suitable precipitants are solvents in which the compound I dissolves only to a slight extent, if at all, at least at temperatures below 25° C. These include in particular aliphatic and cycloaliphatic hydrocarbons such as pentane, hexane, cyclohexane, heptane, petroleum ether and the like. The precipitation/crystallization may be followed by further purification measures.

The process according to the invention affords the compounds I in high yield of generally at least 80% and frequently at least 90%, based on the compound II, and good purities even in the crude product of generally at least 90% without complicated crystallization or other purification measures being necessary. It will be appreciated that further purification measures, for example crystallizations, may be carried out in a manner known per se. Surprisingly, the process according to the invention affords the compound I with a high E/Z isomer ratio of E:Z>4, which is advantageous with regard to the use of the compounds I as insecticide. A further increase in the E/Z ratio can be achieved in a known manner by isomerizing with iodine. The isomerization of the Z isomer of I to the E isomer in the presence of iodine is described in PCT/EP2004/012872 of Nov. 12, 2004, whose disclosure content is incorporated herein by way of reference.

The hydrazone compounds of the general formula II used in the process according to the invention can be prepared in a similar manner to the prior art processes for preparing semicarbazones by reacting a phenyl benzyl ketone of the formula IV with a hydrazide of the formula V, for example in a similar manner to the methods described in J. Am. Chem. Soc. 75, 1953, p. 2259-2261, J. Org. Chem. 55, 1990, p. 1070-1076 and Synthesis, 1985, p. 1048-1051.

To this end, it has been found to be advantageous when the reaction of the benzyl phenyl ketone IV with the hydrazide V is undertaken in the presence of an acid. Examples of acids which are suitable in principle are sulfuric acid, organic sulfonic acids, in particular aromatic sulfonic acids such as p-toluenesulfonic acid and benzenesulfonic acid, aliphatic sulfonic acids such as methanesulfonic acid and trifluoromethanesulfonic acid, aromatic carboxylic acids such as benzoic acid and substituted benzoic acids such as 4-trifluoromethylbenzoic acid, and also aliphatic carboxylic acids having preferably from 1 to 4 carbon atoms, for example acetic acid and propionic acid. Preferred acids are carboxylic acids, in particular aliphatic carboxylic acids having preferably from 1 to 4 carbon atoms and especially acetic acid. In general, the acid will be used in an amount of from 0.01 to 2 mol per mole of compound IV and in particular in an amount of from 0.05 to 1.5 mol/mol of compound IV. In the case of sulfonic acids, preference is given to catalytic amounts, i.e. in amounts of less than 1 mol per mole of compound IV, in particular in the range from 0.01 to 0.5 mol/mol and especially in the range from 0.05 to 0.2 mol/mol. In the case of carboxylic acids, larger amounts of acids may also be used, for example from 0.1 mol to 2 mol and especially from 0.5 to 1.5 mol, per mole of compound IV.

To react the ketone IV with the hydrazide V, the compounds will preferably be used in a molar IV:V ratio in the range from 1:2 to 1.1:1, in particular from 1:1.5 to 1:1 and more preferably from 1:1.3 to 1:1.05.

In a preferred embodiment of the invention, a hydrazide of the formula V is used where R is $C_1$-$C_4$-alkoxy and in particular methoxy. Such hydrazides V are also referred to hereinbelow as carbazate V.

Ketone IV is advantageously reacted with the hydrazide V at temperatures in the range from 10 to 100° C., in particular from 20 to 80° C. The reaction pressure is of minor importance for the success of the reaction and may be, for example, in the range from 500 mbar to 10 bar. The reaction is preferably carried out in the region of atmospheric pressure, for example in the range from 0.9 to 1.2 bar. The reaction time required for the reaction is generally in the range from 4 h to 72 h and in particular in the range from 8 h to 60 h.

The reaction may in principle be carried out in substance. However, preference is given to reacting the hydrazide of the formula V with the ketone IV in an organic solvent. Preferred organic solvents are $C_1$-$C_4$-alkanols, in particular methanol and ethanol, and also aromatic solvents, in particular alkylbenzenes such as toluene, xylenes, ethylbenzene, cumene (2-propylbenzenes), cymenes (isopropyltoluenes) and mesitylene, and also chlorobenzene, 1,2-, 1,3- and 1,4-dichlorobenzene and mixtures of these solvents.

The water formed in the reaction of the ketone IV with the hydrazide V may be removed from the reaction mixture during the reaction in a manner known per se, for example by separation as an azeotrope with the solvent used in the reaction. However, the water of reaction may also remain in the reaction mixture.

For the reaction, ketone IV and hydrazide V may be contacted together in a manner which is per arbitrary se. In general, the ketone IV and the hydrazide V will be initially charged in a reaction vessel, if appropriate together with the solvent desired, and then the desired reaction conditions will be established. However, the majority or entirety of ketone IV and hydrazide V, if appropriate in a solvent, may also be introduced into the reaction vessel under reaction conditions, or one of the components IV or V may be initially charged and the majority of the other components added in the course of the reaction.

The compound II can be isolated from the reaction mixture in a manner known per se. If the reaction has been carried out in a solvent, the reaction mixture will generally be concentrated and/or cooled, and/or a precipitant will be added. Suitable precipitants are solvents in which the compound II dissolves only to a limited extent, if at all, at least at temperatures below 25° C. These include in particular aliphatic and cycloaliphatic hydrocarbons such as pentane, hexane, cyclohexane, heptane, petroleum ether, methanol, ethanol, alkylbenzenes and the like. The precipitation/crystallization may be followed by further purification measures. When the reaction is carried out as preferred in an alcohol, in particular in methanol or ethanol or in an alkylbenzene, it is generally unnecessary to add a precipitant.

The reaction described here, of the ketone IV with the hydrazide V, affords the compounds II in high yield of generally at least 80% and frequently at least 95%, based on the compound II, and very high purities of frequently at least 90% and in particular at least 95%, without complicated crystallization or other purification measures being required. It is therefore possible to dispense with isolation of the compound II from the reaction mixture.

A preferred embodiment of the invention therefore relates to a process in which, in a first step, the hydrazone derivative of the formula II is prepared by reacting ketone IV with the hydrazide V and the compound II is subsequently reacted with the aniline compound III without isolation. To this end, it may be advantageous when a portion or the entirety of the solvent used to prepare the hydrazone II is removed and substituted by another solvent. However, the reaction of the hydrazone II with the aniline III in particular will be carried out in the solvent used to prepare the hydrazone II.

The ketones IV used to prepare the hydrazone II and processes for their preparation are disclosed by the prior art, for example by WO 00/18714, JP 4168826 and WO 03/091203.

The examples which follow serve merely to illustrate the invention and are not to be interpreted in a restrictive manner.

The purities and isomer ratios reported were determined by means of high-pressure liquid chromatography (HPLC) via the area ratios of the particular peaks.

In connection with the NMR spectra, s is a singlet, d is a doublet and t is a triplet. MS stands for mass spectrum and IR for IR spectrum.

EXAMPLE 1

Preparation of the Hydrazone of the Formula II where R is Methoxy, $R^1$ is 3-$CF_3$ and $R^2$ is 4-CN Variant A:

18.8 g (0.21 mol) of methyl carbazate (HN—NH—C(O)—$OCH_3$) and 57.8 g (0.20 mol) of 3-trifluoromethylphenyl 4-cyanobenzyl ketone (compound IV where $R^1$=3-$CF_3$ and $R^2$=4-CN) were dissolved in 700 ml of methanol at 20° C. Subsequently, 2 ml of concentrated sulfuric acid were added, the mixture was stirred at 20° C. for 2 days and the precipitated solid was isolated. This was washed with 100 ml of methanol and dried in a drying cabinet at 50° C./10 mbar. In this way, 62.6 g (corresponding to a yield of 86.7% of theory) of the hydrazone II {$R^1$=3-$CF_3$, $R^2$=4-CN} were obtained with a purity (HPLC) of 99.6%.

Melting point: 171° C.

MS (EI): m/e=361 ($M^+$ ion)

IR: 2245 $cm^{-1}$ (CN); 1704 $cm^{-1}$ (C=O)

$^1$H NMR (DMSO): δ/ppm=3.8 (s, 3H); 4.5 (s, 2H); 7.4 (d, 2H); 7.64 (t, 1H); 7.7 (d, 1H), 7.8 (d, 2H); 8.0 (d, 1H); 8.15 (s, 1H); 10.95 (s, 1H)

$^{13}$C NMR (DMSO): δ/ppm=31.77 (t); 52.19 (q); 109.30 (s); 118.64 (s); 122.51 (d); 124.01 (s; C/F coupling const.: 272.3 Hz); 125.30 (d); 129.16 (d, 2C); 129.24 (s); 129.61 (d); 130.25 (d); 132.51 (d, 2C); 138.07 (s); 142.11 (s); 146.45 (s); 154.58 (s)

Variant B:

7.3 g (0.025 mol) of 3-trifluoromethylphenyl 4-cyanobenzyl ketone and 2.4 g (0.025 mol) of methyl carbazate (97%) were reacted in the presence of 2.0 g of acetic acid in 50 g of xylene at 50° C. for 24 h. After cooling to 20° C., the precipitated solid was removed, washed with 10 g of xylene and dried in a drying cabinet at 50° C./10 mbar. In this way, 8.0 g (corresponding to a yield of 88.1% of theory) of the hydrazone II {$R^1$=3-$CF_3$, $R^2$=4-CN} were obtained with a purity (HPLC) of 99.9%.

EXAMPLE 2

Preparation of the Compound I where $R^1$ is 3-$CF_3$ and $R^2$ is 4-CN and $R^3$ is 4-$OCF_3$ Variant A:

In a reaction vessel having a distillation column, 7.2 g (0.02 mol) of the hydrazone from Example 1 and 3.9 g (0.022 mol) of 4-trifluoromethyoxyaniline were combined in 100 g of xylene and the mixture was heated to reflux. Within 7 h, 80 g of a mixture of methanol and xylene were distilled off with a high reflux ratio. The reaction mixture was cooled slowly to 60° C. and 5 g of cyclohexane were added at this temperature. Subsequently, the mixture was cooled further to 10° C. The precipitated solid was removed, washed with 10 g of cyclohexane and dried in a drying cabinet at 80° C./10 mbar. In this way, 9.4 g of the title compound (corresponding to a yield of 92.2% of theory) were obtained in the form of an isomer mixture having a purity of 98.1% (81.2% E isomer and 16.9% Z isomer).

Variant B:

In a reaction vessel having a distillation column, 21.6 g (0.06 mol) of the hydrazone from Example 1 and 11.7 g (0.066 mol) of 4-trifluoromethoxyaniline were combined in 300 g of xylene and the mixture was heated to reflux. Within 7 h, 12 g of a mixture of methanol and xylene were distilled off at a high reflux ratio. To crystallize the product, a further 234 g of xylene were distilled off. The mixture was cooled slowly to 60° C., 75 g of cyclohexane were added at this temperature and the mixture was subsequently cooled further to 10° C. The precipitated solid was removed, washed with 30 g of cyclohexane and dried in a drying cabinet at 100° C./10 mbar. In this way, 28.0 g of the title compound (corresponding to a yield of 84.6% of theory) were obtained in the form of an isomer mixture having a purity of 91.5% (77.4% E isomer and 14.1% Z isomer).

What is claimed is:

1. A process for preparing phenylsemicarbazone compounds of the formula I

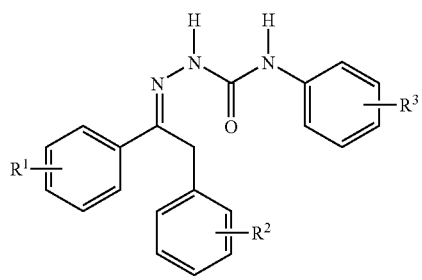

where $R^1$ and $R^2$ are each independently hydrogen, halogen, CN, $C_1$-$C_4$-alkyl, $C_1$-$C_4$-alkoxy, $C_1$-$C_4$-haloalkyl or $C_1$-$C_4$-haloalkoxy, and $R^3$ is $C_1$-$C_4$-alkoxy, $C_1$-$C_4$-haloalkyl or $C_1$-$C_4$-haloalkoxy, comprising the reaction of a hydrazone compound of the general formula II where R is $C_1$-$C_4$-alkoxy, amino, $C_1$-$C_4$-alkylamino or di($C_1$-$C_4$alkyl)amino, and $R^1$, $R^2$ are each as defined above

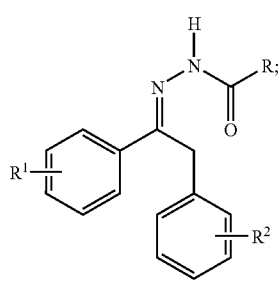

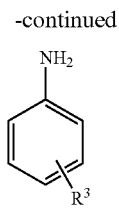

with an aniline compound of the general formula III where $R^3$ is as defined above.

2. The process according to claim 1, wherein R is $C_1$-$C_4$-alkoxy.

3. The process according to claim 2, wherein R is methoxy.

4. The process according to claim 1, wherein R is amino, methylamino, ethylamino or dimethylamino.

5. The process according to claim 1, wherein the aniline compound III and hydrazone compound of the general formula II are used in a molar II:III ratio in from 1:1.5 to 1.5:1.

6. The process according to claim 1, wherein the hydrazone compound of the formula II is provided by reacting a benzyl phenyl ketone of the formula IV

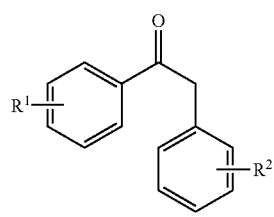

where $R^1$, $R^2$ are each as defined in claim 1, with a hydrazide of the formula V

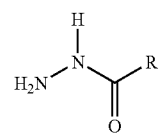

where R is as defined in claim 1.

7. The process according to claim 6, wherein R in formula V is $C_1$-$C_4$-alkoxy.

8. The process according to claim 7, wherein the reaction of the benzyl phenyl ketone IV with the hydrazide V is undertaken in the presence of an acid.

9. The process according to claim 6, wherein the hydrazone compound of the general formula II is reacted with the aniline compound III without isolation.

10. The process according to claim 6, wherein $R^1$ in the formulae I, II and IV is meta-trifluoromethyl, $R^2$ in the formulae I, II and IV is para-CN and $R^3$ in the formulae I and III is para-trifluoromethoxy.

* * * * *